United States Patent [19]

Forte et al.

[11] Patent Number: 4,664,786
[45] Date of Patent: May 12, 1987

[54] PROCESS FOR THE SEPARATION OF HYDROCARBONS FROM A MIXED FEEDSTOCK

[75] Inventors: Paulino Forte, Yonkers; José A. Vidueira, White Plains, both of N.Y.

[73] Assignee: Union Carbide Corporation, Danbury, Conn.

[21] Appl. No.: 839,633

[22] Filed: Mar. 14, 1986

Related U.S. Application Data

[63] Continuation-in-part of Ser. No. 713,844, Mar. 20, 1985, abandoned.

[51] Int. Cl.$^4$ .................. C10G 7/08; C10G 7/00; B01D 3/38
[52] U.S. Cl. ................... 208/356; 208/353; 208/355; 208/321; 203/25; 203/96; 203/DIG. 14
[58] Field of Search ............. 208/311, 313, 321, 353, 208/355, 356, 363, 365, 366; 203/25, 96, 97, DIG. 14

[56] References Cited

U.S. PATENT DOCUMENTS

| | | | |
|---|---|---|---|
| 3,037,062 | 5/1962 | Gerhold | 208/321 |
| 3,151,046 | 9/1964 | Larson | 203/96 X |
| 3,179,708 | 4/1965 | Penisten | 208/313 |
| 3,494,861 | 2/1970 | Munro | 208/353 |
| 3,702,295 | 11/1972 | Thompson | 208/321 |
| 4,175,034 | 11/1979 | Thompson | 208/356 |
| 4,260,476 | 4/1981 | Vidueira et al. | 208/365 X |
| 4,261,814 | 4/1981 | Pfeifer | 208/356 |
| 4,415,443 | 11/1983 | Murphy | 208/355 |

FOREIGN PATENT DOCUMENTS

| 35168 | 3/1977 | Japan | 203/DIG. 14 |
|---|---|---|---|
| 706439 | 12/1979 | U.S.S.R. | 203/DIG. 14 |

*Primary Examiner*—Glenn Caldarola
*Attorney, Agent, or Firm*—Morris N. Reinisch

[57] ABSTRACT

In a steam distillation process for the recovery of aromatic hydrocarbons wherein there is (i) a primary flash zone at the top of the distillation zone in which rich solvent is flashed and/or (ii) provision for the removal of side cut distillate vapors from about the middle of the distillation zone, the improvement comprising (a) heat exchanging flashed rich solvent vapors or side-cut distillate vapors with stripping water to provide stripping water vapors and stripping water at at least about the boiling point of water; (b) passing the stripping water vapors from step (a) to a steam ejector; (c) passing the stripping water from step (a) to a motive steam generator wherein the stripping water is vaporized under pressure; (d) passing the stripping water vapors from step (c) to the steam ejector referred to in step (b); and (e) passing the stripping water vapors, introduced into the steam ejector in accordance with steps (b) and (d), to the lower half of the distillation zone.

6 Claims, 1 Drawing Figure

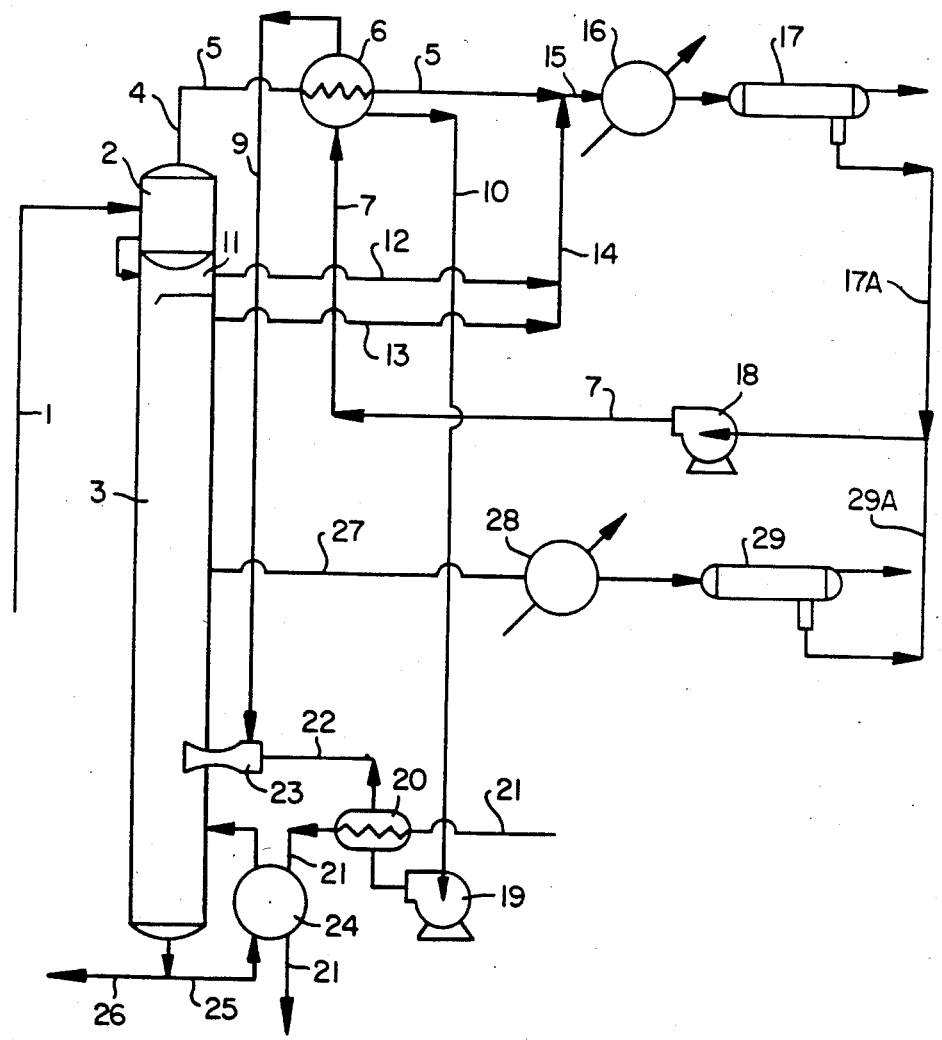

PROCESS FOR THE SEPARATION OF HYDROCARBONS FROM A MIXED FEEDSTOCK

This is a continuation-in-part of U.S. Ser. No. 713,844, filed Mar. 20, 1985, abandoned, herein incorporated by reference.

TECHNICAL FIELD

This invention relates to a steam distillation process for the recovery of hydrocarbons from a mixed feedstock.

BACKGROUND

The benzene-toluene-$C_8$ aromatic fraction (known and hereinafter referred to as BTX) is now well established as a premier raw material in the manufacture of petrochemicals and as a desirable component in boosting octane ratings in gasoline. Many processes have been proposed for the separation of BTX, e.g., the process proposed in U.S. Pat. No. 3,714,033, which is incorporated by reference herein.

There is an industrial need for BTX, which is available in high proportion, e.g., greater than 30 percent by weight, in a wide variety of hydrocarbon feedstocks such as reformed gasolines; coke oven light oils; and cracked gasolines. These feedstocks also contain both aliphatic and cycloaliphatic hydrocarbons. Since the individual hydrocarbon compounds which make up these feedstocks are well known, they will not be discussed extensively; however, it can be pointed out that the major components of the feedstocks used herein are hydrocarbons with boiling points ranging from 25° C. to 175° C. including straight-chain and branched-chain paraffins and naphthenes, such as n-heptane, isooctane, and methyl cyclohexane, and aromatics such as BTX.

The BTX fraction can include benzene, toluene, the $C_8$ aromatics including ortho xylene, meta xylene, paraxylene, and ethyl benzene, and $C_9$ aromatics, which, if present at all, appear in the smallest proportion in relation to the other components.

The solvents used in solvent extraction/steam distillation processes for the recovery of BTX are water miscible organic liquids (at process temperatures) having a boiling point of at least about 200° C. and having a decomposition temperature of at least about 225° C. The term "water-miscible" includes those solvents which are completely miscible over a wide range of temperatures and those solvents which have a high partial miscibility at room temperature since the latter are usually completely miscible at process temperatures. The solvents are also polar and are generally comprised of carbon, hydrogen, and oxygen with some exceptions. Examples of solvents which may be used in the process of this invention are dipropylene glycol, tripropylene glycol, dibutylene glycol, tributylene glycol, ethylene glycol, diethylene glycol, ethylene glycol monomethyl ether, ethylene glycol monoethyl ether, diethylene glycol monomethyl ether, diethylene glycol monoethyl ether, sulfolane, N-methyl pyrrolidone, triethylene glycol, tetraethylene glycol, ethylene glycol diethyl ether, propylene glycol monoethyl ether, pentaethylene glycol, hexamethylene glycol, and mixtures thereof. The preferred group of solvents is the polyalkylene glycols and the preferred solvent is tetraethylene glycol.

Additional solvents, which may be used alone or together, or with the aforementioned solvents are amides such as formamide, acetamide, dimethylformamide, diethylformamide, and dimethylacetamide; amines such as diethylenetriamine and triethylenetetramine; alkanolamines such as monoethanolamine, diethanolamine, and triethanolamine; nitriles such as beta,beta[1]-oxydipropionitrile and beta,beta[1]-thiodipropionitrile; phenol and the cresols; the methyl sulfolanes; sulfoxides such as dimethyl sulfoxide and diethyl sulfoxide; lactones such as gamma propiolactone and gamma-butyrolactone.

The apparatus used in the process both for extraction and distillation is conventional, e.g., an extraction column of the multi-stage reciprocating type containing a plurality of perforated plates centrally mounted on a vertical shaft driven by a motor in an oscillatory manner can be used as well as columns containing pumps with settling zones, sieve trays with upcomers, or even a hollow tube while the distillation can be conducted in a packed, bubble plate, or sieve tray fractionating column. Counter-current flows are utilized in both extraction and distillation columns.

Heat exchangers, decanters, reservoirs, solvent regenerators, condensers, compressors, and pumps as well as various extractors other than the main extractor can also be used to complete the system. The other extractors are preferably single stage mixer-settlers, but can be any of the well known types. Again, all of this apparatus is conventional off the shelf equipment commonly used in extraction/distillation processes.

The solvent is used as an aqueous solution containing water in an amount of about 1 percent to about 10 percent by weight based on the weight of the solvent and preferably containing water in an amount of about 2 percent to about 6 percent by weight.

Generally, to accomplish the extraction, the ratio of solvent (exclusive of water) to feedstock in the extractor is in the range of about 4 to about 8 parts by weight of solvent to one part by weight of feedstock. This broad range can be expanded upon where nonpreferred solvents are used. A broad range of about 3 to about 12 parts by weight of solvent to one part by weight of feedstock and a preferred range of about 5 parts to about 7 parts of solvent per part of feedstock can be used successfully for the solvent of preference and other like solvents. In final analysis, however, the ratio is selected by the technician based on experience with the particular feedstock and depends in part upon whether high recovery or high purity is being emphasized.

The reflux to the extraction zone, an important part of the process, is generally made up of about 20 percent to about 50 percent by weight aliphatics having from 5 to 7 carbon atoms and about 50 percent to about 80 percent by weight aromatics, both based on the total weight of the reflux. The ratio of reflux to feedstock in the extraction zone is, generally, maintained in the range of about 0.5 to about 1.5 parts by weight of reflux to one part by weight of feedstock and preferably about 0.5 to about 1.0 part by weight of reflux to one part by weight of feedstock, but, again, is selected by the technician just as the ratio of solvent to feedstock. The reflux aliphatics pass into the extract rather than being taken overhead with the raffinate and are recycled to the extractor from the reflux decanter.

The temperature in the extraction zone is maintained in the range of about 100° C. to about 200° C. and is preferably in the range of about 125° C. to about 150° C., especially for the solvent of preference.

The pressure in the extraction zone is maintained in the range of about 75 psig to about 200 psig. As is well know in the art, however, one selected pressure is not maintained throughout the extraction zone, but, rather, a high pressure within the stated range is present at the bottom of the zone and a low pressure, again within the stated range, is present at the top of the zone with an intermediate pressure in the middle of the zone. The pressures in the zone depend on the design of the equipment and the temperature, both of which are adjusted to maintain the pressure within the stated range.

The temperature at the top of the distillation zone, which, in terms of the apparatus used, may be referred to as a distillation column or stripper, is at the boiling point of the mixture of aromatics present in the zone while the temperature at the bottom of the stripper is generally in the range of about 135° C. to about 200° C.

The pressure at the top of the stripper, an upper flash zone in this case, is in the range of about 20 psig to about 45 psig. In a lower flash zone just beneath the upper flash zone and connected thereto, the pressure is in the range of about 10 psig to about 25 psig and is about 10 or 20 psig lower than the pressure in the upper flash zone. The pressure in the rest of the distillation zone is maintained in the range of about 15 psig to about 25 psig with some variation throughout the zone.

The steam or steam/water mixture brought into the bottom of the distillation zone enters at a temperature of about 100° C. to about 150° C. and is under a pressure of about 15 psig to about 25 psig. The total water and/or steam injected into the distillation column is in the range of about 0.1 part to about 0.5 part by weight of water to one part by weight of aromatics in the zone and preferably in the range of about 0.1 part to about 0.3 part by weight of water to one part by weight of aromatics. The water used for the stripping steam is usually called stripping water. A small amount of water is present in liquid form in the distillation zone dissolved in the solvent.

Typically, in solvent extraction/steam distillation processes, the feedstock is preheated and then introduced to the main extractor at about the middle tray. An aqueous solvent solution (known as lean solvent) enters at the top tray of the extractor and percolates down the column removing aromatics from the feedstock. The raffinate, essentially free of aromatics, leaves the top of the column. Provisions are made for the recovery of solvent and any remaining aromatics from the raffinate as well as the water which is used to wash it. In the lower half of the extractor, the solvent solution of aromatics comes into countercurrent contact with a reflux liquid, which enters the extractor below the bottom tray. The reflux percolates up the lower half of the extractor progressively dissolving in and purifying the solvent solution of aromatics. The extract (known as rich solvent) leaves the bottom of the extractor and enters the stripper (or distillation zone) at an upper flash chamber. Part of the extract flashes on entering the flash chamber and is taken overhead in vapor form and the other part of the extract passes as a liquid into a lower flash chamber. Again, part of the extract, flashes overhead and the balance of the extract (at least about 80 percent by weight) percolates down the column into the fractionation zone where it comes into countercurrent contact with the stripping vapors, i.e., steam, and more vapors are generated. A part of the vapors rises to the top of the column where it mixes with flash vapors to form the overhead distillate. The overhead distillate provides reflux for the extractor. After the rich solvent descends about halfway down the column, it becomes essentially free of aliphatics. At this point, a vapor side-cut distillate is removed. The side cut distillate is separated into its aromatics and solvent/water components, the aromatics being recovered and the solvent and water being recycled into the system. Stripping water from the side cut distillate and other water from the system is returned to the bottom of the stripper as steam or a steam/water mixture. The bulk of the solvent and water leaves the bottom of the stripper. A portion of this solution is directed to a reboiler where it is vaporized and then returned to a point below the bottom tray of the stripper to provide heat therefor. The balance of the solvent/water solution is recycled to the top tray of the main extractor.

There are many specific variations of the above process, each of which seeks either to reduce apparatus requirements, i.e., capital expenditure, or energy consumption, or make more effective use of process components while meeting purity specifications.

SUMMARY OF THE INVENTION

By this invention steam distillations can be conducted with reduced energy consumption by the indirect heat exchange of the overhead from the distillation zone with water at a pressure lower than that in the distillation zone. This lower pressure is sufficient to enable water to be vaporized and is maintained by passing the vaporized overhead to the low pressure port of a fluid ejector through which a higher pressure stream entering the distillation zone, such as a feed stream or steam, is passed. Additional reduction of energy consumption can be achieved by passing the unvaporized water from the heat exchanger to a motive steam generator and using the motive steam as the fluid for the fluid ejector.

Not only can the processes of this invention offer reduced energy consumption, but, also, the processes enable the re-use of stripping water. In many steam distillation processes, the stripping water in the overhead from the distillation zone contains minor portions of the components to be separated. Thus, the stripping water may not be suitable for disposal or for use in other process equipment such as steam boilers. The processes of this invention can enable this stripping water to be recycled to the steam distillation zone in an economic and efficient manner in which heat is recovered from the overhead stream and effectively returned to the steam distillation zone. Moreover, the process may be practiced with little capital investment and without undue maintenance because of the use of the fluid ejector to maintain the lower pressure in the heat exchange.

The process may be suitable for various steam distillation operations wherein a substantially water immiscible component is being separated. These separations include the separation of hydrocarbons, essential oils, fatty acids, turpentine, pine oil, camphor, monomers from polymers and the like, and can find application in processes such as acid gas removal processes, the Benfield process, alkanolamine acid gas treating system, and the like.

According to one aspect of the invention, an improvement has been found in a steam distillation process for the recovery of hydrocarbons wherein there is (i) a primary flash zone at the top of the distillation zone in which rich solvent is flashed and/or (ii) provision for the removal of side-cut distillate vapors from about the middle of the distillation zone.

The improvement comprises (a) heat exchanging flashed rich solvent vapors or side-cut distillate vapors with stripping water to provide stripping water vapors and stripping water at at least about the boiling point of water; (b) passing the stripping water vapors from step (a) to a steam ejector; (c) passing the stripping water from step (a) to a motive steam generator wherein the stripping water is vaporized under pressure; (d) passing the stripping water vapors from step (c) to the steam ejector referred to in step (b); and (e) passing the stripping water vapors, introduced into the steam ejector in accordance with steps (b) and (d), to the lower half of the distillation zone.

In another aspect of the invention, an overhead vapor stream from the distillation zone is heat exchanged with stripping water at a temperature which under the pressure of the heat exchanging is at least about the boiling point of water whereby stripping water vapors are produced and passed to a steam ejector. Steam, at a higher pressure, is passed through the steam ejector into the distillation zone whereby the pressure of the heat exchange is lower than the pressure of the steam distillation.

In a further aspect of the invention, a feed stream containing at least one substantially water immiscible component to be separated and an operative stream containing at least one of water and steam are introduced into a steam distillation vessel which is maintained under steam distillation conditions including temperature and pressure to provide a vaporous overhead stream containing the at least one component to be separated and a liquid bottoms fraction. The liquid bottoms fraction is withdrawn from a lower portion of the vessel and the overhead stream is withdrawn from an upper portion of the vessel and is passed through an indirect heat exchanger. The overhead stream is condensed to provide a liquid stream rich in the at least one component to be separated and a water stream. At least a portion of the water stream is passed to the indirect heat exchange as the heat exchange medium and at least a portion of the water stream in the indirect heat exchanger is vaporized at a lower absolute pressure than the pressure in the steam distillation vessel. This vaporized stream is passed to a lower pressure inlet of a fluid ejector through which at least one of the feed stream and at least a portion of the operative stream is passed at a higher absolute pressure into the steam distillation vessel whereby the heat exchange medium side of the indirect heat exchanger is maintained at said lower absolute pressure sufficient to generate steam using heat contained in the overhead stream.

BRIEF DESCRIPTION OF THE DRAWING

The sole figure is a schematic flow diagram of an illustrative embodiment of the subject invention.

DETAILED DESCRIPTION

The main extractor, feedstock, solvent, temperatures, and pressures are as described above except as noted. While subject process can be applied to any steam distillation process, which provides for a primary flash zone and/or side cut distillate vapors, the application of particular interest is a solvent extraction/steam distillation process for the recovery of aromatic hydrocarbons.

Referring to the drawing:

The rich solvent from the extractor (not shown) is at a temperature in the range of about 100° C. to about 150° C. It passes along line 1 to primary flash chamber 2 at the top of stripper 3. Primary flash chamber 2 is maintained at a pressure in the range of about 20 pounds per square inch gauge (psig) to about 60 psig. Part of the hydrocarbon and water in the rich solvent is flashed overhead along line 4 to pass as a vapor through line 5 at a temperature in the range of about 90 to about 140° C. and at a pressure in the range of about 15 psig to about 55 psig entering, prior to its condensation, into stripping water vaporizer (heat exchangers) 6. The stripping water enters vaporizer 6 along line 7 at a temperature in the range of about 35° to about 80° C. As the primary flash vapors condense, the stripping water is heated to about 100° C., the boiling point of water at atmospheric pressure. Part of the stripping water is vaporized at about one atmosphere. The other part remains as a liquid. In the event that vaporizer 6 is operated at less than atmospheric pressure, the boiling point of water will, of course, be reduced accordingly.

The stripping water is split into two streams, the vapor following line 9 and the liquid following line 10. The condensed primary flash vapors proceed along line 5 where they meet vapors from secondary flash chamber 11 and the top of stripper 3 passing along lines 12 and 13, respectively, and combining into line 14. Streams 5, 12, and 13 represent the overhead distillate. Streams 5 and 14 combine and enter stream 15, which is introduced into reflux condenser 16. The vapors are condensed in reflux condenser 16 and the liquid passes into decanter 17 where a hydrocarbon reflux phase is separated from a water phase. The reflux is recycled to the extractor and the water phase is combined with the water phase from decanter 29 and sent to pump 18 for reuse as stripping water. The water phase from decanter 17 is passed along line 17A and the water phase from decanter 29 is passed along line 29A. The stripping water, which is at a temperature in the range of about 35° to about 80° C. is passed from pump 18 along line 7 to stripping water vaporizer 6 as noted above.

The stripping water, at about 100° C., passes through line 10 to pump 19 and thence to motive steam generator 20 where it is converted to high pressure steam with a temperature in the range of about 170° to about 230° C. and at a pressure in the range of about 100 to about 400 psig This is accomplished by introducing steam at a pressure in the range of about 125 to about 450 psig along line 21 into motive steam generator 20. The stripping water steam (or motive steam) from generator 20 then passes along line 22 to steam ejector 23 providing the driving force therefor. The stripping water vapor at 100° C. enters steam ejector 23 along line 9 and is pumped into stripper 3. Essentially all of the steam from steam ejector 23 is pumped into stripper 3.

The content of solvent in the stripping water entering generator 20 is less than about one percent by weight. This small amount of solvent concentrates in generator 20 and is purged out of generator 20 and into stripper 3 by using a purge stream not shown in the drawing.

The steam used in generator 20 continues along line 21 into reboiler 24 where it vaporizes a portion of the lean solvent/water solution passing along line 25 from the bottom of stripper 3. The steam is condensed and leaves the system along line 21 while the lean solvent/water solution vapor is returned to stripper 3 along line 25. The bulk of the lean solvent/water solution from the bottom of stripper 3 passes along line 26 to the top of the main extractor.

The side-cut distillate vapors pass from the middle of stripper 3 through line 27 to condenser 28. The now liquid side-cut distillate then passes into decanter 29 where an aromatics phase is separated from a water phase. The water phase is recycled as stripping water to pump 18 and the aromatics phase is recovered for further distillation and separation.

An alternate procedure (not shown) is to use the side-cut distillate vapors instead of the primary flash vapors. The side-cut distillate vapors, at a temperature in the range of about 90° to about 140° C. and a pressure of about 0 psig to about 20 psig, are introduced into stripping water vaporizer 6. The procedure, then is the same as described for the primary flash vapors.

After the heat is obtained from the side-cut distillate vapors, the remaining vapors pass to condenser 28 and the condensate then continues along line 27. Further, the alternate procedures can be combined, i.e., the heat can be recovered form both the primary flash vapors and the side-cut distillate vapors. To accomplish this, an additional stripping water vaporizer is needed for the side-cut distillate vapors together with additional piping to complete the scheme. The key to the energy recovery is using the primary flash vapors and/or side cut distillate vapors before the vapors expand, i.e., while they are under pressure, the pressure being in the range of about 20 to about 60 psig for the primary flash vapors and about 0 to about 25 psig for the side cut distillate vapors. In order of preference, i.e., achieving the highest heat recovery, the side-cut distillate vapors appears to be first, the use of both primary flash vapors and side cut distillate vapors, second, and the primary flash vapors, third. This order can change, however, depending on the particular case to which the invention is applied. The recovery of heat from the vapors is enhanced by the use of a high flux tubing heat exchanger, which make temperature approaches of about 2° to about 3° C. feasible. The purity of the side-stream distillate vapors makes the stripping water vaporizer a good candidate for a high flux tubing application.

The advantages of subject process are as follows:

1. High energy savings. Further, the higher the stripping water rate used to strip the aromatics, i.e., the higher the aromatic content of the feed, the greater the energy savings obtained.

2. The process is applicable to any distillation column that uses stripping water to remove hydrocarbons (or any other solute) from a solvent.

3. The cost of the stripping water vaporizer and the motive stream generator are offset by the elimination of other heat exchangers required in comparable systems.

4. Steam ejectors are inexpensive as compared to the usual compressors.

The invention is illustrated by the following example (percentages and ratios are by weight):

The process described above and in the drawing is carried out twice in the preferred mode, once using the primary flash vapors (process A) and the other time using the side-cut distillate vapors (process B). The feedstock is characterized as a high severity reformate containing about 63 percent BTX. The lean solvent solution contains about 94 percent tetraethylene glycol and about 6 percent water.

The operating conditions and results are the same for process A and process B except as noted. They are as follow:
temperature of rich solvent entering stripper 3: 138° C.
pressure in primary flash chamber: 35 psig
temperature of primary flash vapors: 129° C.
temperature of side-cut distillate vapors: 126° C.
pressure of side cut distillate vapors (before expansion): 10 psig
temperature in stripper 3: 156° C.
pressure in stripper 3: 12 psig
temperature of stripping water vapors in line 9: 100° C.
pressure of stripping water vapors in line 9: 1 atmosphere
temperature of stripping water in line 7: 49° C.
temperature of stripping water in line 10: 100° C.
pressure of steam entering line 21: 200 psig
pressure of motive steam in line line 22: 125 psig
feedstock rate (pounds per hour): 116,198
solvent solution to feedstock ratio: 5.2
reflux to feedstock ratio: 0.78
stripping water rate (pounds per hour): 29,336
primary flash vapors (pounds per hour): 17,341
side-cut distillate vapors (pounds per hour): 92,747
Recoveries, i.e., percent of recovery based on amount in feedstock:
  benzene: 99.97
  toluene: 99.78
  xylene: 98.55
  cumene: 84.48
Impurities (parts per million by weight): 632
reboiler duty for Process A ($10^6$ BTU's per hour) 55.1
reboiler duty for Process B ($10^6$ BTU's per hour) 51.0
estimated energy saved in Process A ($10^6$ BTU's per hour). 8.15
estimated energy saved in Process B ($10^6$ BTU's per hour) 12.0
estimated energy reduction in Process A (percent): 12
estimated energy reduction in Process B (percent): 19
Note: Energy savings and percentage reduction are based on a comparison with a process run using the same steps and conditions except that the primary flash vapors and side-cut distillate are not used to heat the stripping water. Instead a rich solvent/stripping water heat exchanger is used to provide heat for the stripping water.

We claim:

1. In a steam distillation process for the recovery of hydrocarbons wherein there is (i) a primary flash zone at the top of the distillation zone in which rich solvent is flashed and/or (ii) provision for the removal of side cut distillate vapors from about the middle of the distillation zone, the improvement comprising (a) heat exchanging flashed rich solvent vapors or side cut distillate vapors with stripping water to provide stripping water vapors and stripping water at at least about the boiling point of water; (b) passing the stripping water vapors from step (a) to a steam ejector; (c) passing the stripping water from step (a) to a motive steam generator wherein the stripping water is vaporized under pressure; (d) passing the stripping water vapors from step (c) to the steam ejector referred to in step (b); and (e) passing the stripping water vapors, introduced into the steam ejector in accordance with steps (b) and (d), to the lower half of the distillation zone.

2. The process defined in claim 1 wherein the steam distillation process is a solvent extraction/steam distillation process for the recovery of aromatic hydrocarbons.

3. A steam distillation process comprising introducing into a steam distillation vessel (i) a feed stream containing at least one substantially water-immiscible component to be separated and (ii) a stripping stream containing at least one of water and steam; operating said steam distillation vessel to provide a vaporous overhead stream containing the at least one component to be separated and a liquid bottoms fractions wherein the bottoms fraction is withdrawn from a lower portion of the vessel and the overhead stream is withdrawn from an upper portion of the vessel; passing the overhead stream through an indirect heat exchanger and thereafter condensing said overhead stream to provide a liquid stream rich in the at least one component to be separated and a water stream; passing at least a portion of said water to the indirect heat exchanger as the heat exchange medium; vaporizing at least a portion of the water stream in said indirect heat exchanger at a lower absolute pressure than the pressure in the steam distillation vessel; and passing the steam generated in the indirect heat exchange vessel to a low pressure inlet of a fluid ejector through which at least one of the feed stream and at least a portion of the stripping stream is passed at a higher absolute pressure into the steam distillation vessel whereby the heat exchange medium side of the indirect heat exchanger is maintained at said lower absolute pressure sufficient to generate steam using heat contained in the overhead stream.

4. The process of claim 3 wherein the operative stream passed through the fluid ejector comprises steam.

5. In a steam distillation process for the recovery of at least one substantially water-immiscible component from a feed stream in a distillation zone containing water and steam, the improvement comprising (a) heat exchanging an overhead vapor stream from the distillation zone with stripping water at a temperature which under the pressure of the heat exchanging is at least about the boiling point of water to vaporize said stripping water into stripping water vapors; (b) passing the stripping water vapors from step (a) to a steam ejector; and (c) passing steam through the steam ejector into the distillation zone whereby the pressure of the heat exchanging in step (a) is lower than the pressure of the steam distillation due to the pressure reduction provided by said steam ejector step (b).

6. The process of claim 5 wherein unvaporized stripping water from step (a) is passed to a motive steam generator wherein the stripping water is vaporized under pressure and this vaporized water is passed to the steam ejector of step (b).

* * * * *